(12) United States Patent
Danielsson

(10) Patent No.: US 6,240,157 B1
(45) Date of Patent: May 29, 2001

(54) TECHNIQUE AND ARRANGEMENT FOR TOMOGRAPHIC IMAGING

(75) Inventor: Per-Erik Danielsson, Linköping (SE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/228,219

(22) Filed: Jan. 11, 1999

(30) Foreign Application Priority Data

Jan. 14, 1997 (SE) .................................................. 9700072
Feb. 10, 1997 (SE) .................................................. 9700437
Jan. 13, 1998 (WO) .................................. PCT/SE98/00029

(51) Int. Cl.$^7$ ........................................................ A61B 6/00
(52) U.S. Cl. .................................. 378/15; 378/4; 378/65
(58) Field of Search ................................... 378/15, 4, 65

(56) References Cited

U.S. PATENT DOCUMENTS

| | | | |
|---|---|---|---|
| 4,712,178 | * 12/1987 | Tuy et al. ............................. | 378/901 |
| 5,394,452 | * 2/1995 | Swerdloff et al. ...................... | 378/65 |
| 5,548,627 | * 8/1996 | Swerdloff et al. ........................ | 378/4 |
| 5,907,593 | * 5/1999 | Hsieh et al. ............................. | 378/4 |
| 5,999,587 | * 12/1999 | Ning et al. ............................... | 378/4 |

* cited by examiner

Primary Examiner—David V. Bruce
Assistant Examiner—Pamela R. Hobden
(74) Attorney, Agent, or Firm—John F. Vodopia

(57) ABSTRACT

Complete helical cone-beam scanning and non-redundant data acquisition are obtained for three-dimensional tomographic imaging of arbitrary long objects. The minimum sized two-dimensional detector window is bounded by two consecutive turns of the helix. The ray source exposes all object points during a rotation of exactly 180 degrees when seen from the points themselves. Only one-dimensional filtering is employed in the reconstruction. Rebinning to parallel beams, as seen along the axis of rotation, allows for especially simple procedures without any need for pre-weighting or magnification factors. As a special case, the invention is applicable to helical fan-beam scanning with one-dimensional detector arrays.

11 Claims, 15 Drawing Sheets

TECHNIQUE AND ARRANGEMENT FOR TOMOGRAPHIC IMAGING

BACKGROUND OF THE INVENTION

1. Field of the Invention

This invention relates to complete helical cone-beam scanning and non-redundant data acquisition for three-dimensional imaging of arbitrarily long objects.

2. Description of Related Art

A two-dimensional detector 11 and a point-shaped ray source (e g X-ray) S are assumed to move synchronously around the object in a helical trajectory as shown in FIG. 1. In a medical tomograph the helical source movement is achieved by translating the patient through the rotating source-detector gantry with constant speed. Two-dimensional projections are acquired (detected) at arbitrarily short intervals along the trajectory. The detector 16 consists of a large number of sensors (detector elements) which are evenly spaced and placed in a plane or, as in FIG. 1, on the surface of the helix cylinder 12. Although the rotation axis 14 is normally horizontal in medical tomographs, rather than vertical as in FIG. 1, we will adopt the following convention. In the sequel, vertical means a direction parallel to the rotation axis 14 (the z-axis) in FIG. 1, while horizontal means a direction parallel to the xy-plane 15.

A projection consists primarily of intensity measures for the incoming rays to a detector element. The logarithms of these primary data represent the sum of the attenuation along the rays, i.e. line integrals over the three-dimensional attenuation function f we want to retrieve. But to be able to reconstruct f from its projections in a correct way, all points in the object have to be fully exposed and the projection data utilized in a balanced way. Thus, if back-projection is used for the reconstruction, projections from all projection angles must be available and brought in with the correct weight to obtain what is called exact reconstruction. Also, the projection data have to be filtered correctly to compensate for the inherent low-pass filtering in the projection-back-projection procedure.

In the literature several mathematically exact methods have been proposed for reconstruction from cone-beam projections. In most cases these methods demand that the object is of finite extension, i.e. restricted in size, so that its total projection never falls outside the available detector. Unfortunately, this requirement is not realistic in most cases of computer tomography, e.g. when one is to reconstruct a full body, or long objects in general. Traditionally, 1D-detector arrays are made large (wide) enough to cover the object across its maximum width. However, for several reasons, it is out of question to extend these 1D-detectors to 2D-detectors, which cover the patient from head-to-toe. Instead, in the foreseeable future, available 2D-detectors will be used to cover and record projections of a section of a long object.

Today, three-dimensional volume data are reconstructed slice-by-slice. The patient is translated slowly (typically 2 mm/sec) while the X-ray source and a one-dimensional detector array are synchronously and continuously rotated at speeds of around 1 r/sec. Relative to a patient which is not moving, the source and detector are then performing a helical movement with very low pitch, say, 2 mm. The reconstruction employs a modified versions of traditional 2D-reconstruction methods for circular scanning of a single slice. However, with the given numbers, it takes approximately 100 sec to fetch data for a 200 mm long section of the body. During this time, due to breathing and other body functions, the body is not fully at rest which blurs the reconstructed object. A second drawback is that the anode of the X-ray tube is subjected to severe strain and extreme temperatures during longer exposure times.

In a 1D-detector system the major part of the generated photons are collimated away without being utilized, while a 2D-detector system is able to utilize a substantial part of these otherwise wasted photons. Hence, by using a 2D-detector with, say, n parallel 1D-detectors in the above example, the velocity can be increased to 2n mm/sec and the scanning time reduced to 100/n sec. Alternatively, speed can be traded for strain on the X-ray source so that, for instance, if the photon flow is halved, the velocity is more moderately increased to n mm/sec and the scanning time reduced to 200/n sec. However, in any case it is no longer possible to perform the reconstruction using conventional 2D-methods since the projection rays are no longer, not even approximately, in the same plane during one turn of the source trajectory.

Circular Source Trajectory

A well-known method for inexact reconstruction from cone-beam projections taken along a circular path was proposed in [Feld84]. The 2D-detector is placed on a planar surface and extended horizontally to cover the width of the object. The width of the object and its distance to the source defines the maximum fan-angle $\gamma_{max}$ of the source-detector system. In the vertical direction the planar detector is limited by two horizontal lines. Along the vertical axis where these lines are closest to the source we find the maximum cone-angle. The image reconstruction consists of the following steps taken for each detector recording. All corrections of geometrical and radiometric nature, including the ever necessary logarithm computation have been left out here for the sake of brevity.

1. Pre-weighting of the recorded detector data with a factor that is proportional to the cosine of the angle between the central ray and the ray that originated the detected value.
2. Filtering with traditional ramp-filtering techniques along each horizontal detector row.
3. Back-projection along the original ray in which process the filtered detector value is multiplied with a so called magnification factor which depends on the distance between the ray source and the object point to receive a contribution from the ray.

This method gives perfect results for image slices in, or close to the mid-section of the object. For slices which have been subjected to more oblique rays at higher cone angles, the image quality deteriorates.

Helical Source Trajectory. Non-exact Methods

Extensions of [Feld84] to helical source paths were first proposed by [Wang93]. Here, the planar 2D-detector is given a vertical extension large enough to ascertain that every point is exposed to the source at least once for every projection angle during a full 360 degree source rotation. The effect of this requirement is that for any given projection angle an object point will be exposed by the source from various numbers of source positions; at least one but often many more, depending on the given fan-angle, cone-angle and detector size. This has to be taken into account during the back-projection. Hence, [Feld84] is employed in [Wang93] but augmented with the following rule.

3a. During the back-projection, for a certain projection angle, among all possible source positions which illuminate an object point, contributions are accepted only from the position which is closest to the actual point in the z-direction.

A way to achieve a more efficient and balanced exposure of the object points was proposed in [Scha96]. Here, the detector is located (wrapped) onto the surface of the source cylinder 41, which in FIG. 2 is seen to be centered in S. The radius of this cylinder equals the source-detector distance, which is different from the radius R of the helix cylinder 12. The helix cylinder is coaxial with the object cylinder in FIG. 1 which is defined by the maximum object width r. In [Scha96] the detector is limited in the vertical direction by two horizontal circles (cross-sections) of the source cylinder 41. However, it is not quite clear what the minimum or optimal height is to be recommended for the detector. In the horizontal direction the detector is limited by two vertical lines, set to let the detector cover the object cylinder. In the following we may use FIG. 1 to clarify some prior art such as this.

The main novelty in [Scha96] is the introduction of complementary projections. These are projection data captured at the source cylinder 41, but sorted and resampled (rebinned) with respect to where the rays from the source are reaching the helix cylinder 12. Assume for the moment that the source is moving along the helix 16 while the object and the helix cylinder is fixed. All rays from various source positions on the same turn, reaching a fixed point on the helix cylinder, is said to be a complementary fan-beam and the projection data for this fan-beam is created during the rebinning. The set of such not quite horizontal and not quite planar fan-beams, with rays fanning out from points on a vertical line on the helix cylinder, constitute a complementary projection. These are employed in the following reconstruction procedure.

1. Pre-weighting of the recorded detector data with a factor that is proportional to the cosine of the angle between the central ray in the projection and the ray that originated the detected value.
2. Re-binning to complementary projections.
3. Filtering of the original as well as the complementary projections with traditional ramp filtering techniques along each horizontal detector row. Because of the non-planar detector this filter is slightly different from the filter employed in [Feld84].
4. For each projection angle, filtered projection data are back-projected along the rays. The values are multiplied with magnification factors which depend on the distance between the point and ray source. All such values, from original as well as complementary cone-beam source positions, are averaged into one single contribution that is accumulated to the object point.

We notice that the detector arrangement in [Scha96] does not secure a perfectly balanced exposure of the object points. During the back-projection event, for each rotation angle, there is a similar situation as in [Wang93] where the object points are exposed from one or several source positions. The difference is that in [Scha96] all these projection data from both original and complementary projections are utilized and averaged together during the backprojection.

[Scha97] proposes another reconstruction technique that is claimed to be more computationally efficient. The detector system is identical to the one in [Scha96] with two horizontal truncating circles on the surface of the source cylinder 41. The reconstruction consists the following steps.

1. Rebinning to oblique parallel projections.
2. Pre-weighting of the recorded detector data with a factor that is proportional to the cosine of the angle between the ray that originated the detected value and the central ray.
3. Reconstruction of one horizontal slice from generalized projections. The latter can be seen as the result of imaginary projection rays running within the horizontal slice.
   3.1 Computation of Fourier domain contributions to this slice for one generalized projection at every projection angle.
   3.1.1 Computation of Fourier domain contributions for each "detector" position in one generalized projection.
   3.1.1.1. Multiplication of projection data (from all source positions that send oblique rays through the slice in this position) with a pre-computed set of weights, which are Fourier series components derived from an adopted interpolation function.
   3.1.1.2. Summation of the contributions for each Fourier component to obtain a single set, a truncated Fourier transform for each ray in this detector position of this generalized parallel projection.
   3.1.2 Computation of the Fourier transform (FFT) along the projection for all these truncated Fourier components to obtain a kind of truncated 2D Fourier transform contribution for each generalized parallel projection.
   3.1.3. Multiplication of the Fourier transform of this generalized projection with a ramp filter.
   3.2. Merging of filtered data from all projection angles in the 2D Fourier space of the horizontal slice and resampling with a space-invariant interpolation filter.
   3.3. Application of an inverse 2D Fourier transform (FFT).
   3.4. Compensating for imperfect interpolation in the Fourier domain by post-weighting the result with the inverse interpolation function, in accordance with the well known gridding technique.

The first rebinning step is best understood if the source, the detector, and the object 17 is pictured as seen from above. From there, the cone-beams will be seen as fan-beams. The rebinning in step 1 above is equivalent to sorting projection data into sets where data from this point of view are produced not by fan-beams but from parallel beams. The term oblique parallel projections stems from the fact that the rays are parallel when seen from above, but in general non-parallel and oblique to the horizontal plane. To understand the following steps it is now recommendable to imagine a planar, virtual detector 122 as in FIG. 3 placed vertically on the rotation axis in the middle of the object. There are several source positions which produce the rays for this projection. Since the real detector on 41 is truncated horizontally and the source positions are located along the helix 16, the effective area of this virtual detector does not have a left-right symmetric shape. The upper and lower boundaries 131 and 132 are curved and tilted as shown in FIG. 4. This is a difference to the perfectly rectangular shape of the corresponding virtual detector 72 in FIGS. 10A and 10B for the present invention. The net effect is that in [Scha97] a varying number of source positions, generate fan-beams which penetrate a given slice under various oblique angles. All of these contribute to the result in the above ingenious but rather complicated computation steps 3.1.1.1 and 3.1.1.2. In the present invention we will find one and only one such fan-beam.

Helical Source Trajectory. Exact Methods

An exact method for reconstruction of a limited sector, a Region Of Interest (ROI) of a long object was proposed in [Tam95] and [Eber95]. The helical scanning covers the full vertical extension of the ROI but has to be complemented with two circular scans at top and bottom, respectively. The detector is placed on a planar surface, just as in [Feld83] and [Wang93] but the detector window is limited to the area between two consecutive turns of the source trajectory 16 as in FIG. 1. The upper and lower truncating lines on the detector plane are therefore neither horizontal, straight, nor left-right symmetric. The arguments for the specific extension of the detector stem from a well-known completeness condition for Radon planes which carries over to the following reconstruction technique. In essential aspects this method is an outgrowth from [Gra87].

1. From each 2D-projection, partial contributions to the derivative of Radon transform values are computed by means of line integration along a multitude of lines in the planar detector. This requires that we select a specific object point to be the origin of a 3D coordinate system.
2. When the scanning is complete, that is when the helical trajectory has covered the intended target region of the object (ROI), all these partial contributions are sorted and coplanar partial contributions are summed.
3. The result is resampled into a regular grid in the Radon transform space of the ROI of the object function.
4. Filtering with a derivative filter.
5. 3D back-projection which takes place as two consecutive 2D back-projection steps.

Generally speaking, this reconstruction is more complicated and costly than the previous ones. Also, the rhythm of the reconstruction procedure is affected by the chosen size of the ROI. It does not feature an even flow of identical procedures repeatedly taking place for every new projection regardless of the length of the object. The two extra circular scans are highly unwanted since they break the smooth and continuous translation-rotation motion of the helical part. However, the method is optimal in one respect. For a given pitch of the helix it utilizes a minimum sized detector. Citation of a reference herein, or throughout this specification, is not to be construed as an admission that such reference is prior art to the Applicant's invention of the invention subsequently claimed.

SUMMARY OF THE INVENTION AND DETAILED DESCRIPTION OF THE PREFERRED EMBODIMENT

The Invention

The present invention utilizes an optimal, minimum cost two-dimensional detector geometry, characterized by an exposure window which is limited vertically by the two nearest turns of the helical source trajectory. Both the motivation for and the exploitation of this detector window differs greatly from the ones given in [Tam95] and [Eber95]. To explain the specific virtue of this exposure window, we refer again to FIG. 1, which shows a perspective view of a source S, a detector 11 wrapped around the helix cylinder 12 and inside this an object cylinder 13. In the sequel, unless stated otherwise, we assume that the object cylinder is rotating counter-clock-wise as shown around the z-axis and translated upwards in a right-handed helix, while the source S and the detector 11 are fixed in the space (x, y, z).

FIG. 6 shows the arrangement as seen from above, while FIG. 7 shows the detector window unwrapped and rolled out on a plane. Note that FIGS. 1 and 7 are consistent only if the rays in FIG. 7 are understood to be coming from the source towards the viewer. FIG. 2 shows the detector placed on the source cylinder 41 centered in S and having a radius which is twice as large as the helix cylinder 12.

BRIEF DESCRIPTION OF THE DRAWING FIGURES

Figure 1:
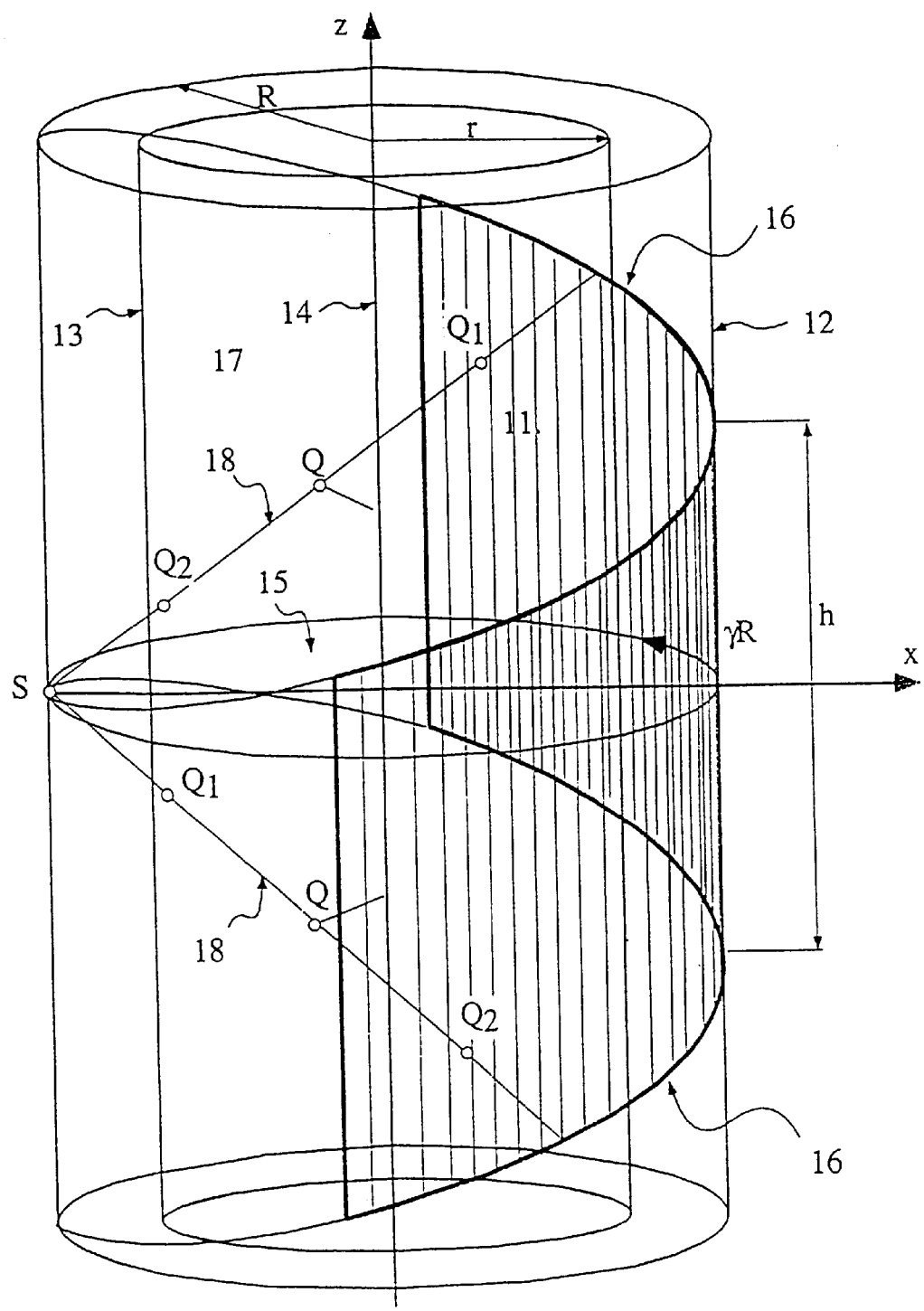
FIG. 1 is a pictorial representation of a two-dimensional detector and point-shaped ray source moving synchronously around an object in a helical trajectory.
Figure 7:
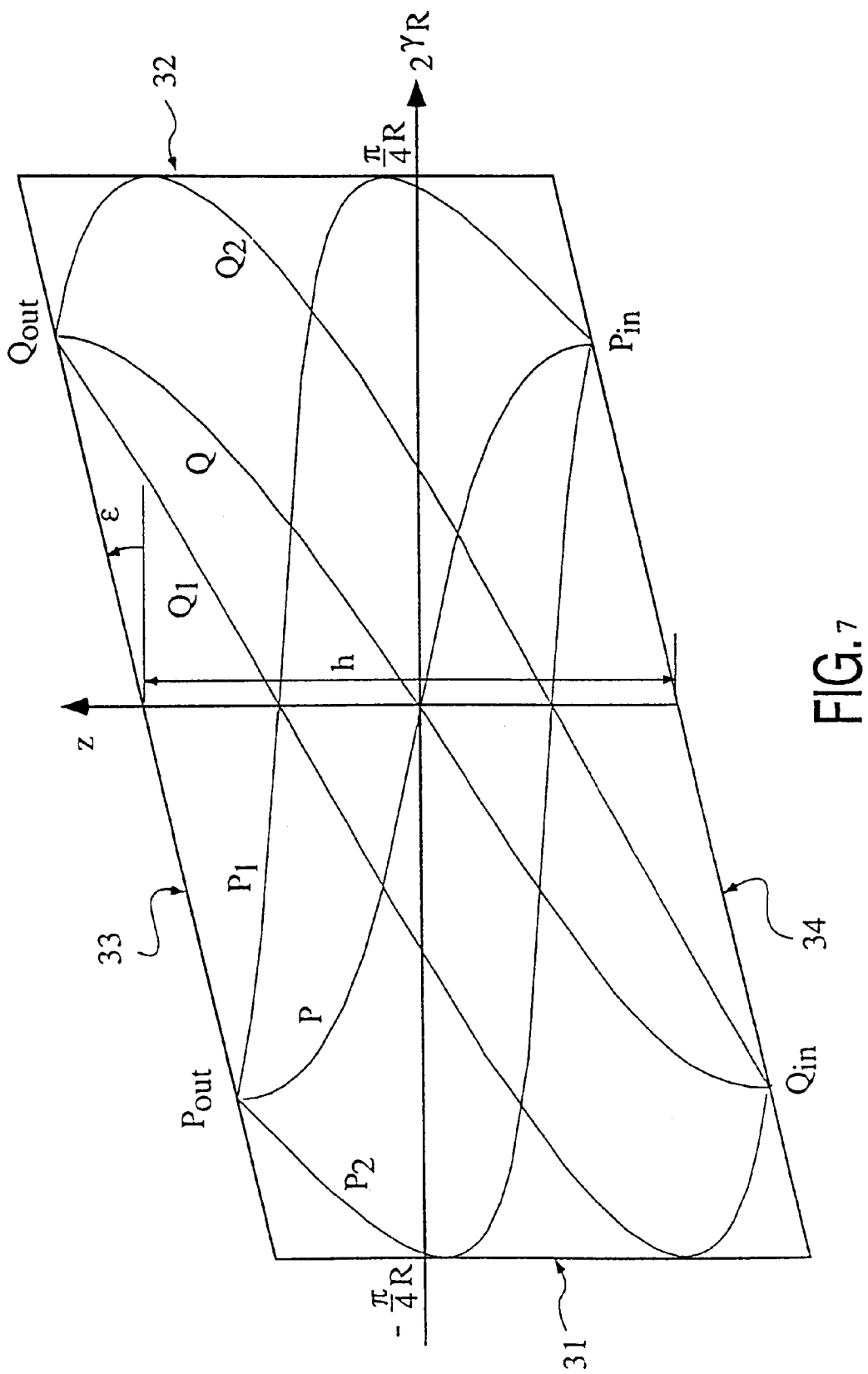
FIG. 7 is a detector surface unwrapped and rolled out on a plane of the detector of FIG. 1.

As mentioned, the 2D-detector 11 in FIG. 1 is wrapped onto the helix cylinder 12. Unwrapped and rolled out on the plane of the sheet, the same detector surface 11 in FIG. 7 is seen to be bounded by four straight lines, two vertical ones 31 and 32, and two slanted ones 33 and 34. Within this area the object 17 is projected, i.e., rays from the cone-beam source reaches active detector elements. Horizontally, this area has to be extended to cover the object cylinder 13, which translates to a certain width, or fan angle $\gamma_{max}$, as seen from the source. As an example we have assumed that this object cylinder has a radius $$r = \frac{R}{\sqrt{2}}$$

where R is the radius of the helix cylinder 12. This means that horizontally on 12 the detector covers a rotation angle of 180 degrees out of 360, and that seen from the source the detector 11 covers a fan angle from −45 to +45 degrees. In principle the detector may be extended to a full turn which then has a fan-angle from −90 to +90 degrees and would allow for an object cylinder that extends all the way to the helix. The slanted lines 33 and 34 are intersecting the cylinder surface 12 at the slope $$\tan \varepsilon = \frac{v}{\omega R} = \frac{h}{2\pi R} \qquad (1)$$

where v is the vertical translation velocity, w is the angular velocity for the rotation, and h is the pitch of the helix.

At the core of the invention is the following property of the detector-exposure window. Every point in a cylindrical long object, with a radius that fits inside the boundaries of the detector window, will be exposed (projected) during a rotation angle which is exactly 180 degrees, seen from the actual point in the object. A conjecture of this new sufficiency condition is that as soon as one point or a set of points (i.e. a part of the long object) has been fully exposed in the above sense, the reconstruction of this part can take place. This is in contradiction to the situation in [Tam95] and [Eber95]] where the whole ROI has to be exposed to make the Radon space complete before the actual reconstruction is commenced.

Figure 6:
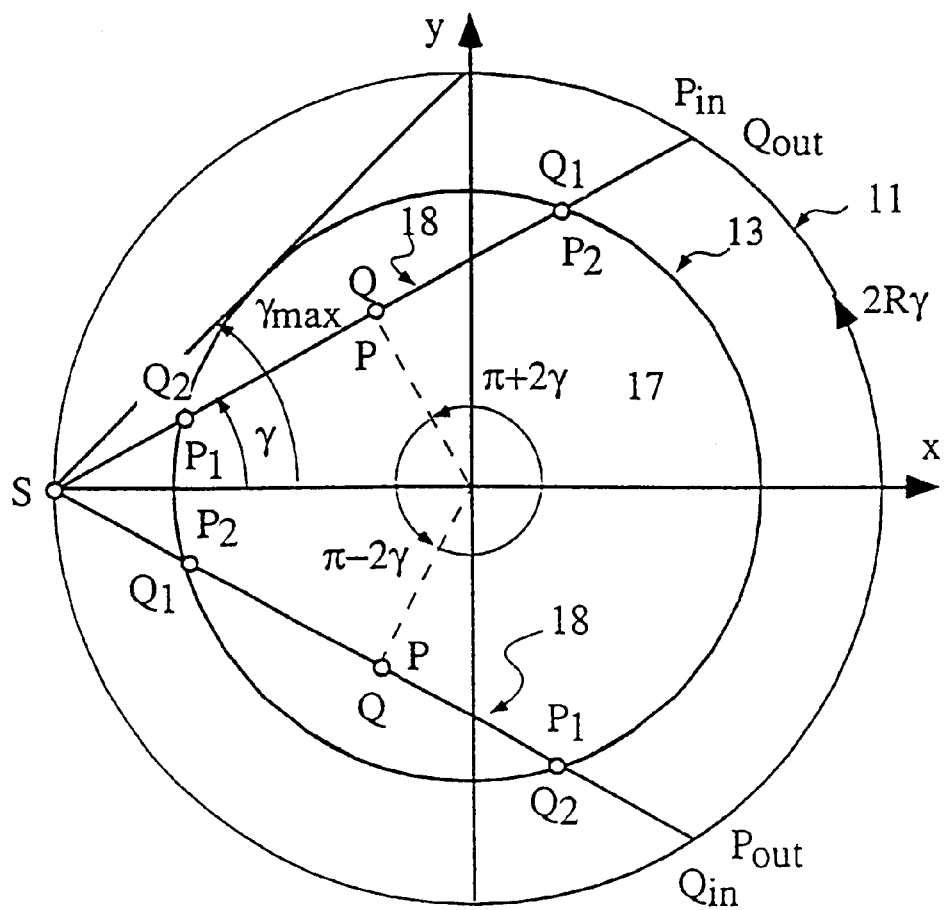
FIG. 6 is a depiction of the arrangement of FIG. 1 as seen from above.

An example of this 180 degree exposure is the line 18 in FIG. 1. It contains the three object points $Q_1$–$Q$–$Q_2$ and it is shown in two positions where the exposure starts and ends, respectively. Note that the end points of this line is sliding and touching the outer cylinder so that during the rotation, both ends will coincide with the source S. Any such line will be called a –line This line is also shown in FIG. 6 in the same two positions.

Assume as before that the object is moving upwards and rotating counter-clockwise when seen from above. In the detector window of FIG. 7 the line $Q_1$–$Q$–$Q_2$ crosses the lower boundary 34 as a single point at $Q_{in}$. After a rotation with the angle $\pi+2\gamma$ around the axis 14 this line will be seen as a single point again from the source leaving the detector at $Q_{out}$ on the upper boundary 33 Clearly, between entrance and exit the source has rotated exactly 180 degrees as seen from any point on this line. Since we have chosen this line quite arbitrarily, the same thing is true for all points in the object which belong to fully exposed –lines. In FIG. 6 and FIG. 7, but not in FIG. 1, we have inserted another –line $P_1$–$P$–$P_2$. In the fixed source-detector system of FIG. 2 this line P enters and exits in positions which are exactly the reverse of the corresponding positions for the line Q. The line P is therefore closer to the source than line Q during its exposure, which takes place during a rotation angle of $\pi-2\gamma$ around the axis 121. The points on line P travels over the detector surface along different and shorter curves as shown in FIG. 7, but seen from any of these points, the source rotates around them exactly 180 degrees.

Every object point belongs to one and only one line. Therefore, the detector system in FIG.1 gives us a complete and perfectly balanced data capture for every point and hence also for the whole object. Furthermore, from the conjecture above follows that it should be possible to reconstruct the object at the same pace as an incremental part (each new set of –lines) of the long object is fully exposed.

Figure 2:
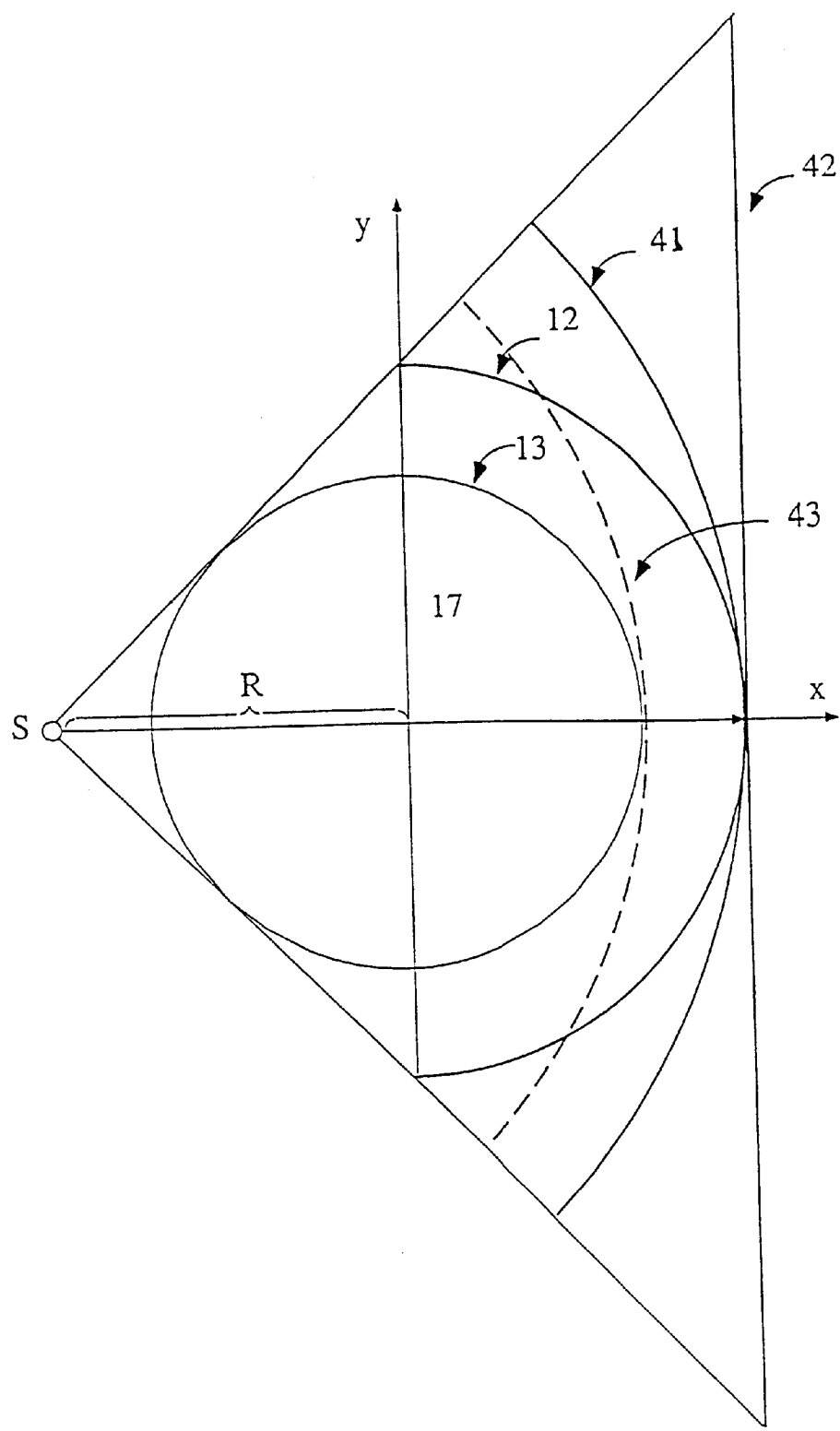
FIG. 2 is a depiction of a detector wrapped onto the surface of the source cylinder, centered in S.

The physical implementation and placement of the detector can of course be made in various ways as indicated in FIG. 2. For instance, it may be placed on the helix cylinder 12 itself, on the source cylinder 41 or on a plane 42. In any case, the detected and utilized data must be restricted to the window defined by FIG. 7.

In our invention, using the same detector data, the elaborate reconstruction in [Tam95] and [Eber95] will be replaced by a much simpler procedure. To describe this procedure, we do not have to limit the ongoing scanning and reconstruction to a predetermined ROI, nor do we have to specify a 3D origin for the process. Instead, scanning and reconstruction is like a constantly ongoing flow, in principle without beginning or end, where each new projection is absorbed and incorporated seamless to the previous result. For this purpose, the following is the general reconstruction procedure for every new projection.

1. Rebinning
2. Pre-weighting (depending on rebinning and detector type)
3. One-dimensional filtering with a ramp-filter across the detector (where the filter design is dependent on rebinning and detector type)
4. Back-projection along incoming ray direction with magnification factors, depending on type of rebinning as well as on detector type: plane, cylindrical, etc.

Figure 8:
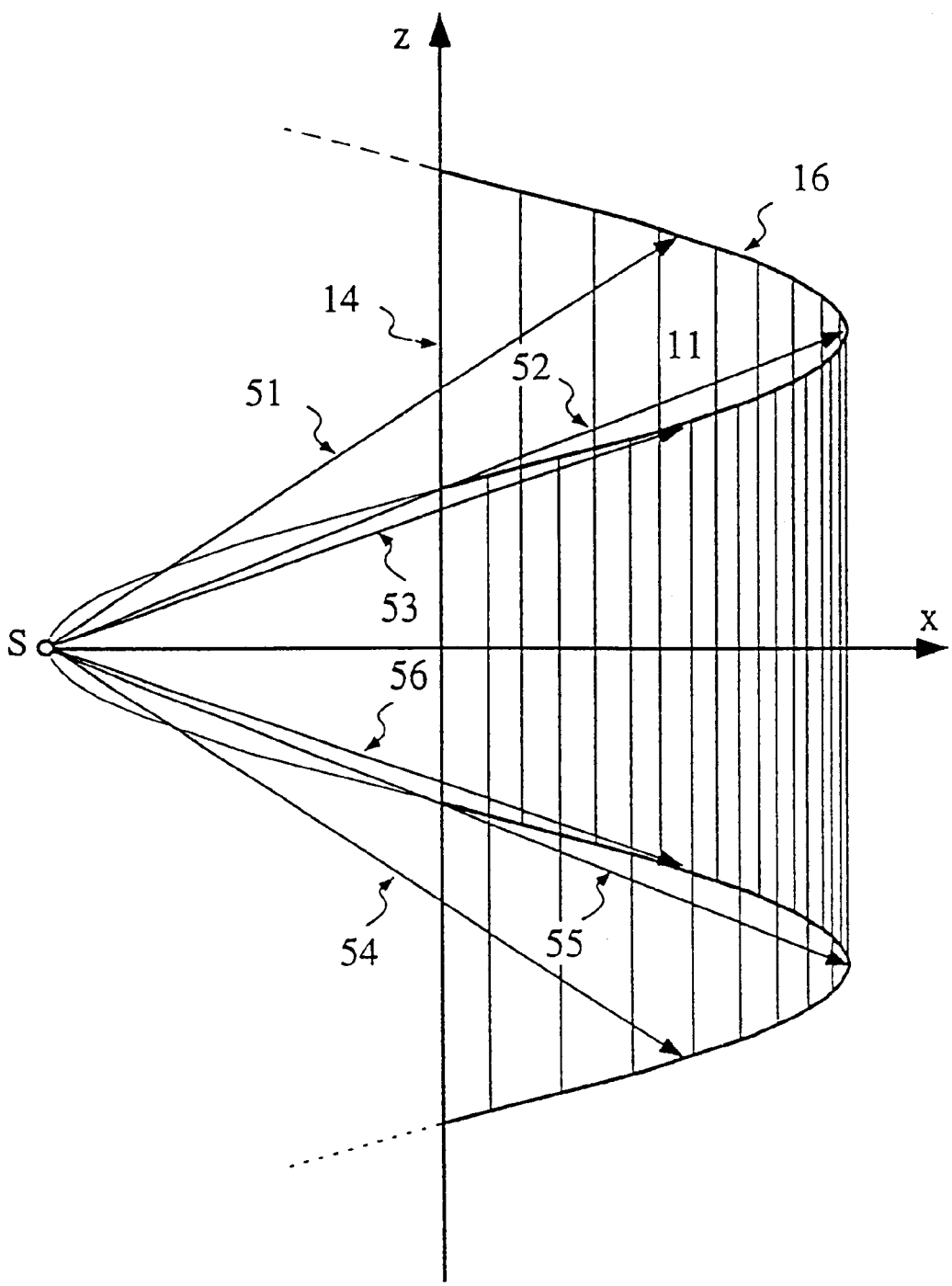
FIG. 8 is a straight side view of the depiction of FIG. 1.

A special case of this procedure is rebinning to parallel projections which we will describe in more detail. FIG. 8 shows a straight side-view of FIG. 1 with six rays 51, 52, 53, 54, 55, and 56 coming from the source S positioned at the x-axis. FIG. 6 shows a view from above where the object is fixed and the source and detector is rotating. With the source in the position $S_\alpha$ we observe three fan-beams 61, 62, and 63 (seen as rays in this view), which comprises the six rays in FIG. 8 and which produce the three projection sets $t(\alpha,\gamma_1)$, $t(\alpha,0)$, $t(\alpha,-\gamma_1)$. The two outer rays are parallel to two other rays, 64 and 65, coming from two other source positions which produce the projections $t(\alpha+\gamma_1, 0)$ and $t(\alpha-\gamma_1, 0)$ respectively Clearly, we may resample our projection data so that data from such parallel fan-beams (seen as rays) are brought together. This can be done with either of the following two equivalent assignments.

$$[p(\alpha+\gamma,\gamma) \leftarrow t(\alpha,\gamma)] \equiv [p(\beta\gamma) \leftarrow t(\beta-\gamma,\gamma)] \qquad (2)$$

Figure 9:
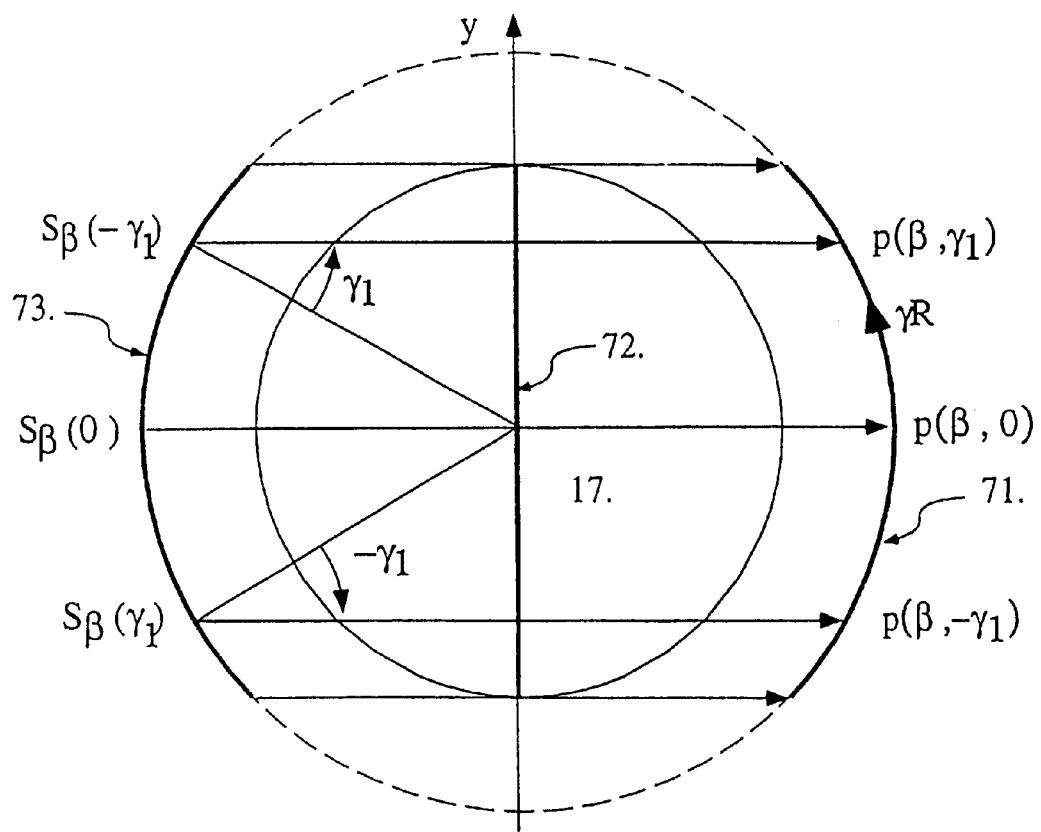
FIG. 9 is a straight top view of the depiction of FIG. 1.
Figure 10A:
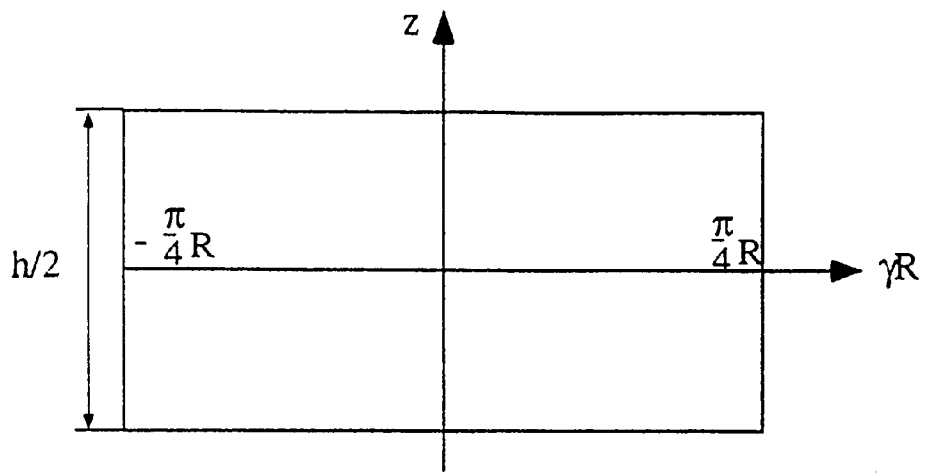
FIGS. 10A, 10B are depictions of a rebinning parallel projection.
Figure 10B:
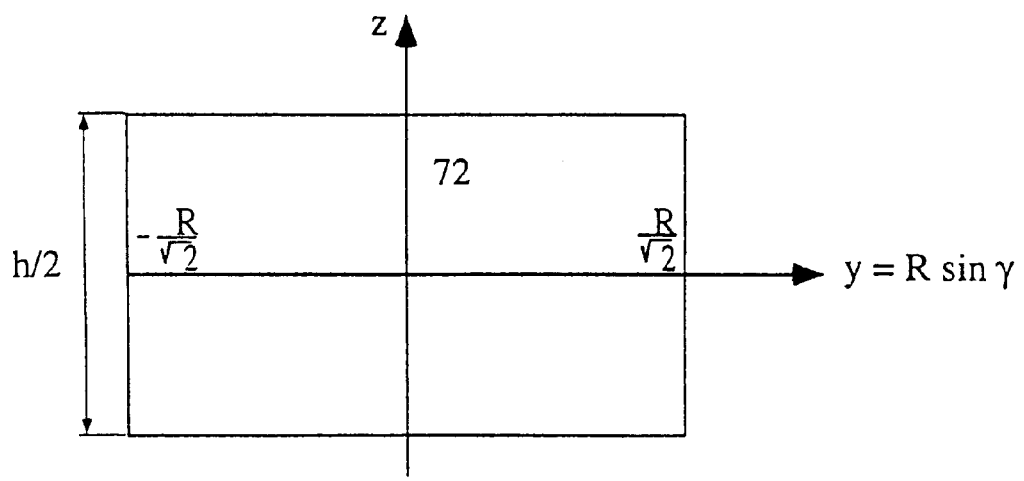

As shown in FIG. 9 we are then free to see the data set p as generated by a parallel beam in the –direction. Without loss of generality, this direction is horizontal in FIG. 9. Perpendicular to these rays we place a virtual detector 72 on a vertical plane.

Figure 5:
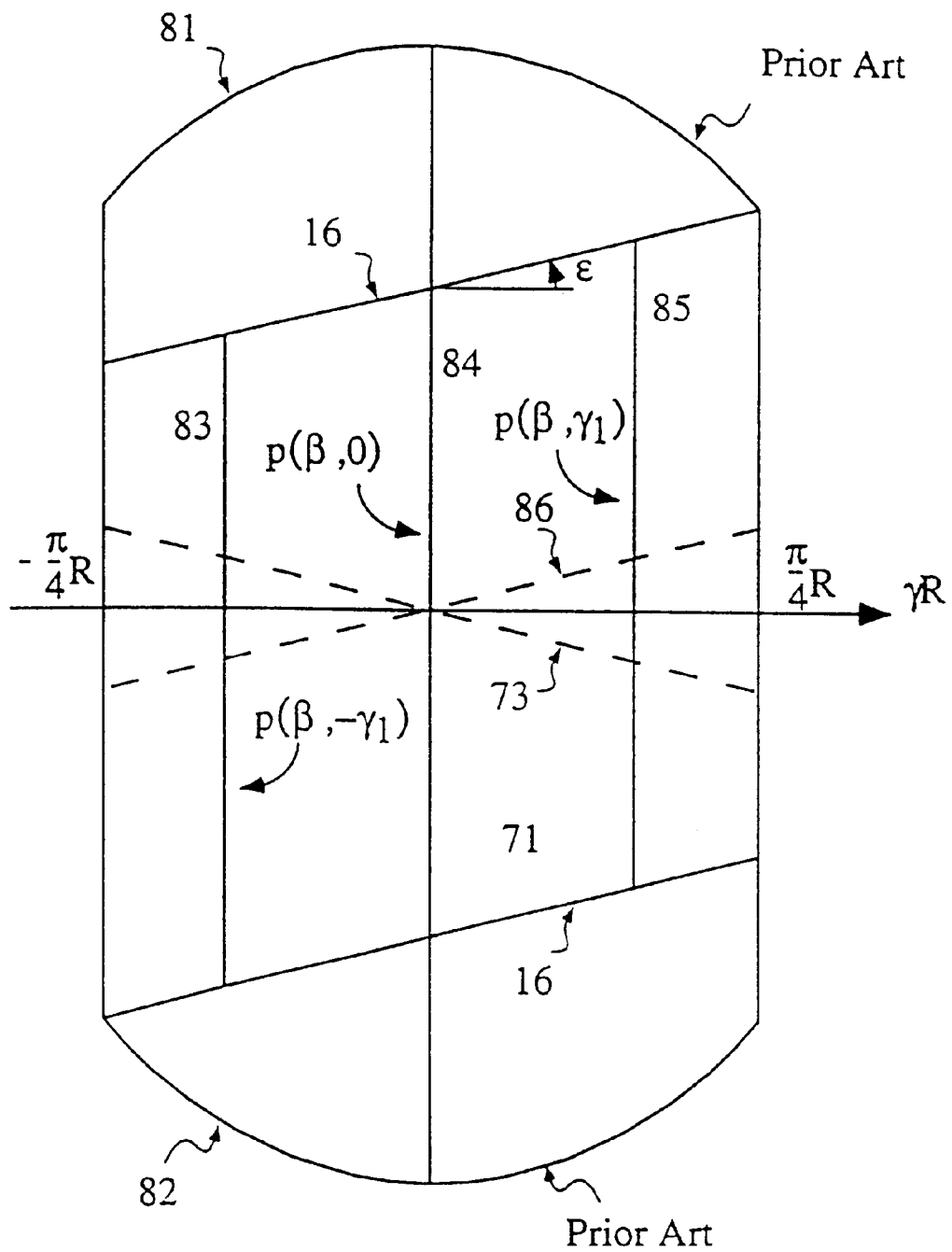
FIG. 5 is a depiction of a parallel projection unwrapped and rolled out onto a 2-D sheet.

The detector window 71 for the parallel projection in FIG. 7 is unwrapped and rolled out into the sheet of FIG. 5. Note that the complete detector positions for the parallel projection are put together from vertical lines 83, 84, and 85 each one stemming from different cone-beam detector positions. The resulting parallel beam detector area has the same slant as the cone-beam detector but is shortened with a factor of two in the –direction. The uppermost and lowermost part of the detector 81 and 82 in FIG. 5 outlines another detector window included here for comparison only. To the best of our understanding, this window corresponds to the minimum size detector in [Scha96] and [Scha97] when mapped onto the helix cylinder 12. For the given pitch=h and the given maximum fan angle $\gamma_{max}$ the height of this detector window is $$\frac{2v(\pi+\gamma_{max})}{\omega R \cos\gamma_{max}} = \frac{h}{\cos\gamma_{max}} \frac{\pi+\gamma_{max}}{\pi} = h\left(\frac{1+\frac{\gamma_{max}}{\pi}}{\cos\gamma_{max}}\right) \qquad (3)$$

This formula indicates that the detector redundancy in [Scha96] and [Scha97] grows rather quickly for increasing fan-angles.

Figure 11:
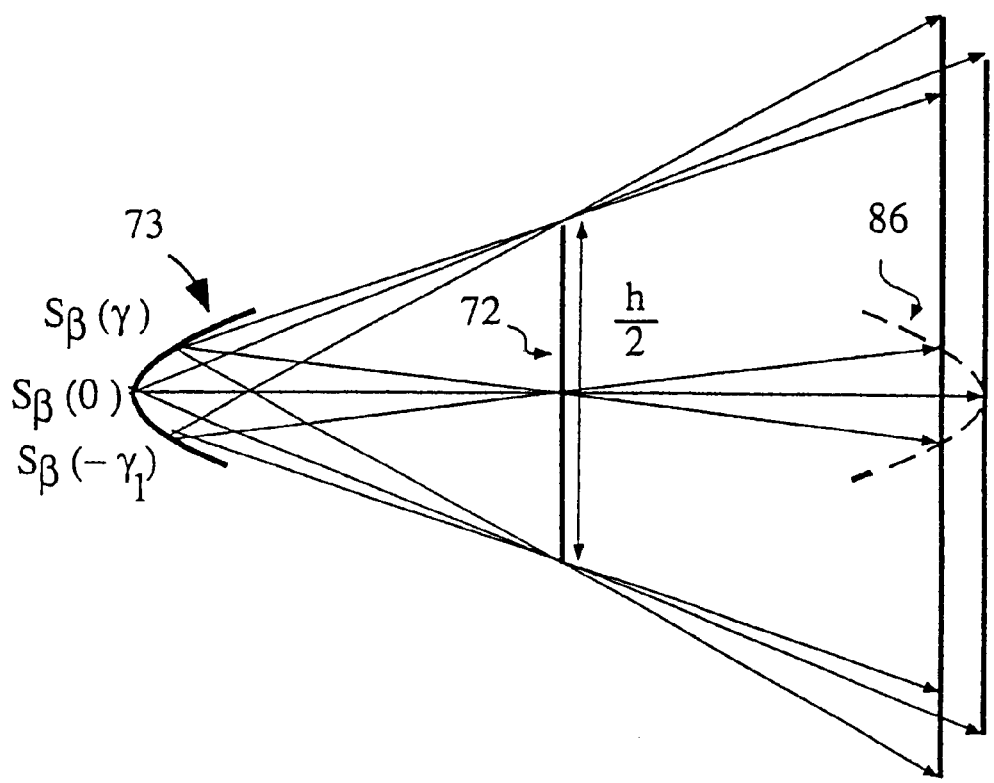
FIG. 11 is a depiction of a generalized projection.
Figures 12A, 12B:
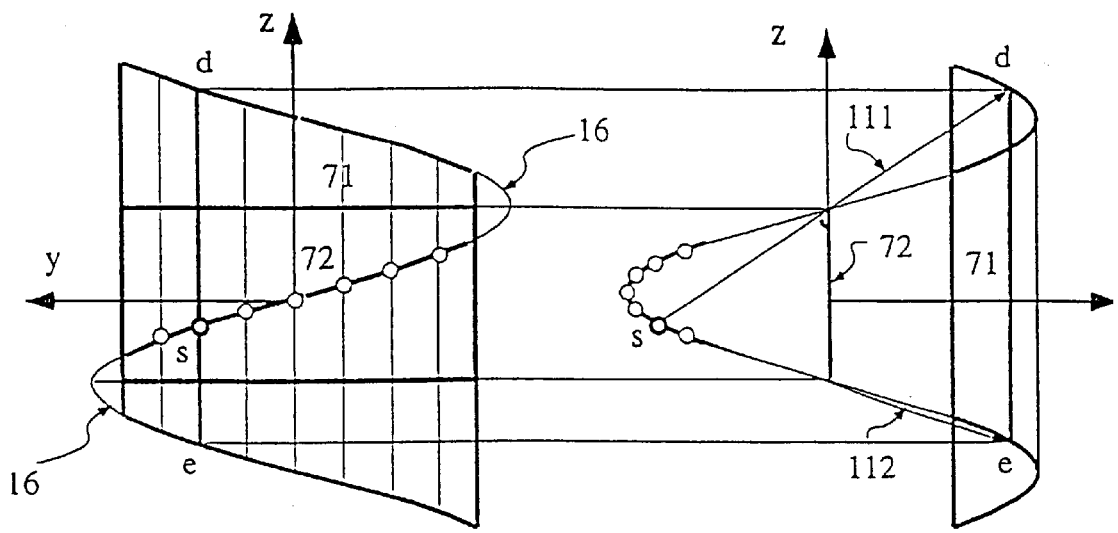
FIGS. 12A, 12B and 12C depict 3 orthogonal views A, B and C of the parallel projection system of the invention.
Figure 12C:
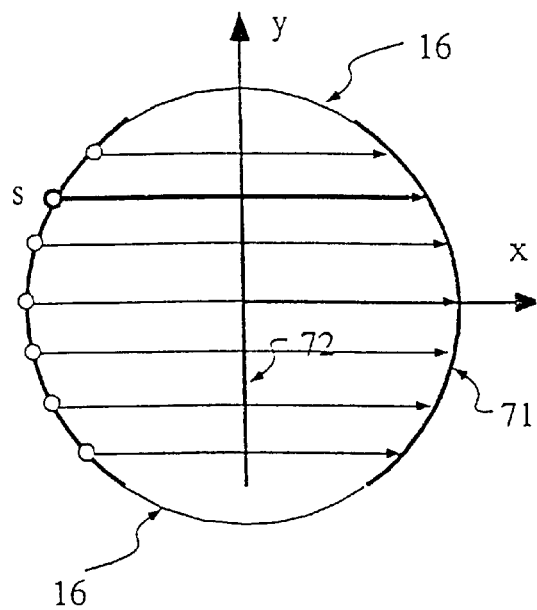
Figure 13:
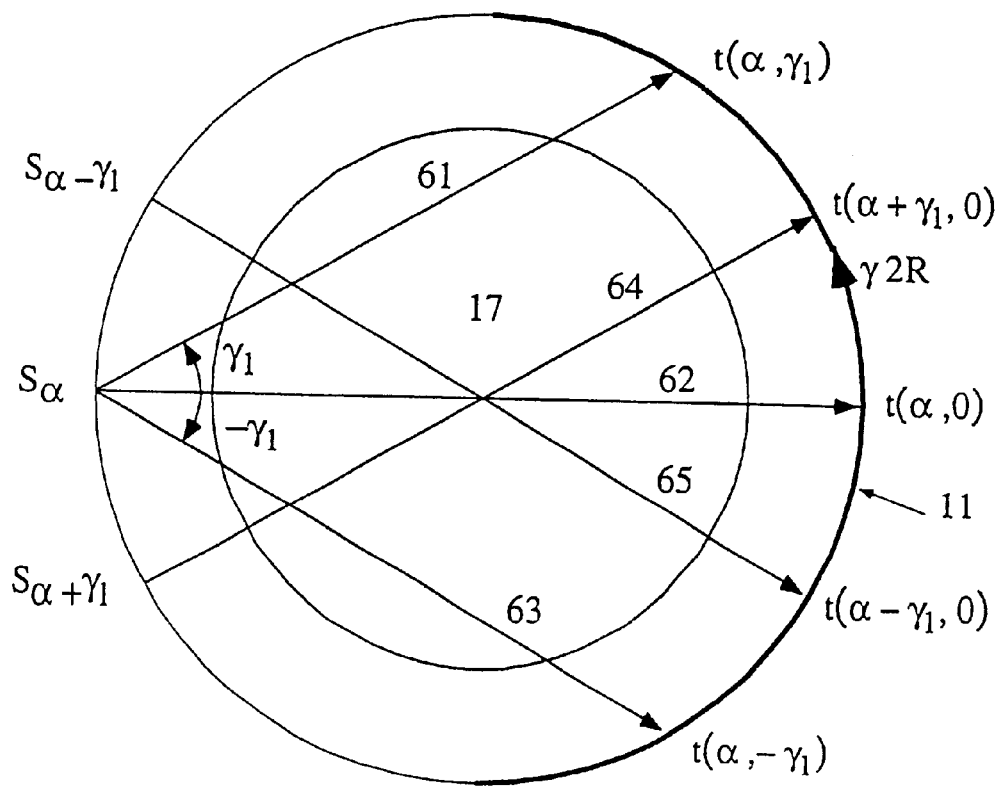
FIG. 13 is a view from above the FIG. 1 representation where the object is fixed and the source and detector are rotating.

The rays in the parallel projection emanate from a set of sources with vertical fan-beams, located on a specific section of the helix. Rolled out in the plane of the sheet this part 73 of the source helix is superimposed on the detector 71 in FIG. 5. It takes the form of a line with the same slant as the detector but with opposite sign. Because of this fact, in the present invention, the virtual detector 72 in the vertical mid-plane is bounded by a perfect rectangle with a width that equals the object cylinder diameter and a height which is exactly half the pitch=h/2. This is illustrated in FIG. 11, where an upward tilt of the source path 73 is exactly compensated for by a downward tilt of the detector. Furthermore, since the distance from the virtual detector 72 to the source is everywhere identical to the distance to the real detector, the real detector height h is always demagnified to exactly h/2 at the virtual detector. FIG. 5 illustrates the second part of the rebinning-resampling procedure, namely from equidistant grid points in R to equidistant grid points in $y=R \sin \gamma$ and y are used as coordinates also for the rebinned parallel projection system.)

The aforementioned property of the virtual detector area being a perfect rectangle is further illustrated in FIG. 11, which shows three orthogonal views A, B, and C of the parallel projection system. Seven source positions are indicated. In A, B we can see the projection from one of the source positions s as a line d-e. Clearly, in view B we see that all the three points s, d, and e are on the helix. Furthermore, the plane of the virtual detector intersects the helix in two points which are exactly halfway between s and d at the upper ray 111 and halfway between s and e at the lower ray 112. Therefore the height of the vertical detector is h/2 with its midpoint on the x-axis for any s. This proofs that the virtual detector is a rectangle with horizontal boundaries.

Thus, using the insight that there is a special detector window which delivers sufficient and non-redundant data, we capture cone-beam projection data on this detector and rebin them into parallel projection data to create an advantageous situation for the actual reconstruction. The complete procedure consists of the following three steps.

1. Rebinning to parallel projections as described by the FIGS. 6, 7, 8, 9, 10, and 11.
2. Filtering with a conventional ramp-filter along horizontal rows in the virtual detector plane.
3. Back-projection in the direction of the original rays using a constant magnification factor.

Figure 4:
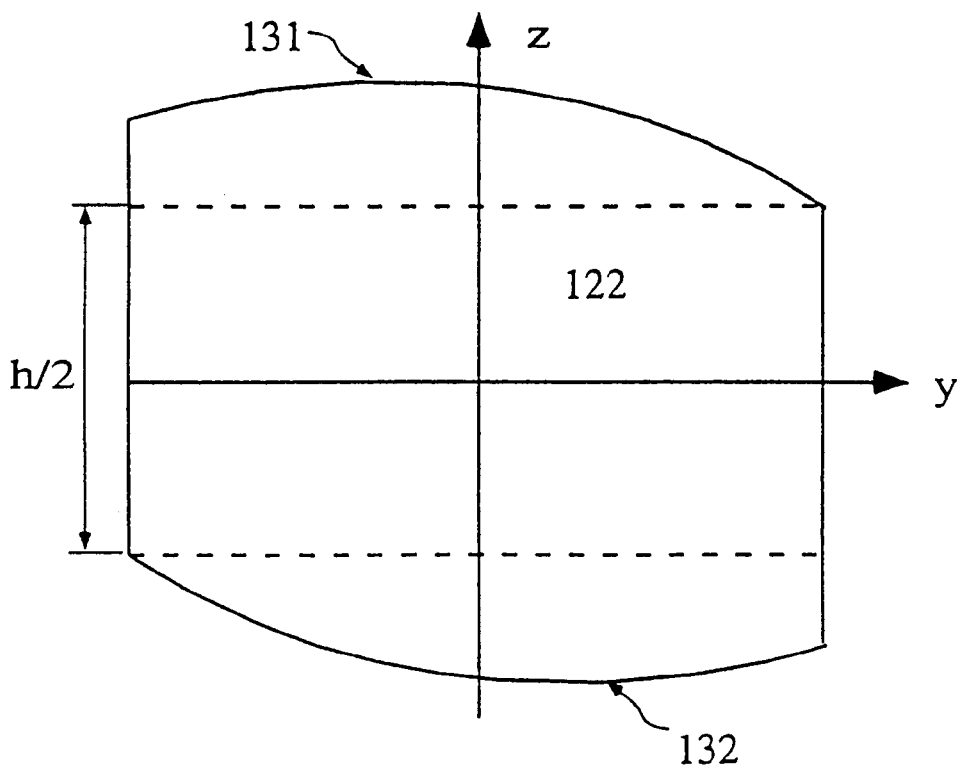
FIG. 4 is a depiction of a virtual detector window.

In the present invention, after parallel rebinning, the one-dimensional filtering takes place along horizontal rows in the virtual detector 72 of FIG. 5. In contrast, in [Scha96] and [Scha97] the filtering takes place along horizontal rows of a real detector placed on the source cylinder, shown as the arc 41 in FIG. 4. FIG. 4 shows this detector mapped onto the virtual detector plane 121. The horizontal rows in the real detector are mapped onto curves in 121 which are neither horizontal nor straight. Clearly, after filtering along such curves in the virtual detector plane rather than along straight horizontal rows as in the present invention the reconstruction result will be rather different.

Figure 3:
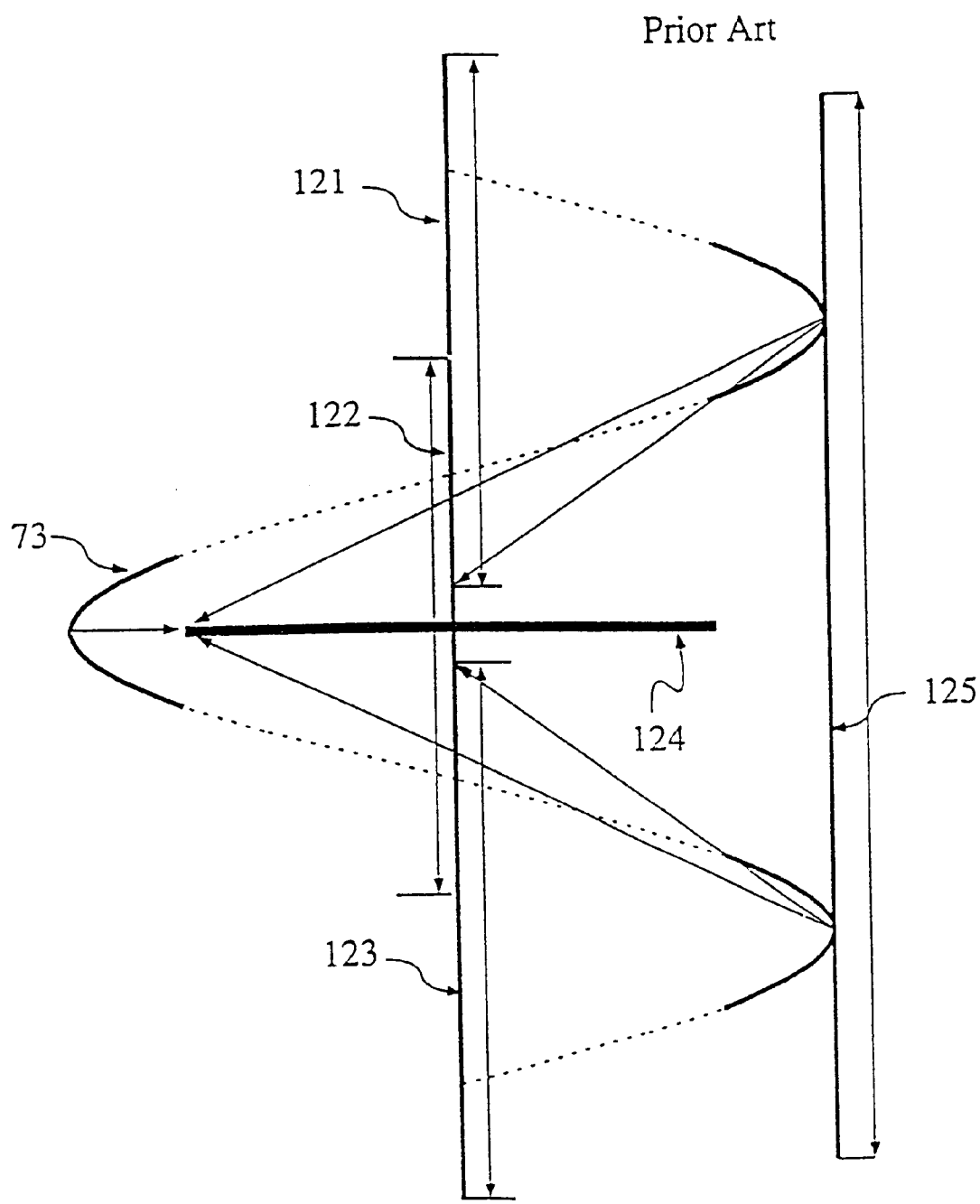
FIG. 3 is a depiction of a vertical section of the parallel scanning system described herein.

Even so, Step 3 in the above procedure may very well be replaced by the version. Reconstruction of one horizontal slice from generalized projections. The simplification is due to the perfectly balanced data capture in the present invention. We know a priori that there is one and only one source position that contributes to each detector position in the generalized projections as shown in FIG. 11. Hence, there is no need to keep track of multiple exposure contributions, since there are neither missing nor redundant data in any projection. The situation is different in [Scha97] which is illustrated in FIG. 3 showing a vertical section of the parallel scanning system. The real detector 125 is much higher than in FIG. 9 so that the virtual detectors 121, 122, and 123 for neighboring half turns overlap vertically. Therefore, in a vertical plane (such as the plane of the sheet) a horizontal slice of the object is partially illuminated not from one but from three source positions on the trajectory. This irregularly distributed redundancy in exposure is also reflected in FIG. 4 which shows the virtual detector window in [Scha97] for the minimum sized detector. The upper and lower boundaries 131 and 132, respectively, are the same as 81, 82 in FIG. 8, although mapped onto the virtual planar detector.

In the most likely physical embodiment of the 2D-detector arrangement proposed in this invention, the detector elements are placed onto the source cylinder 41. See FIG. 2. For moderate cone angles the detector elements are then facing the incoming rays rather straight on. For detectors made to cover high cone angles it might be more appropriate to mount the detector elements on the inside of a sphere centered in S. This would guarantee or at least make it more easy to secure that all detectors are facing the incoming rays correctly.

FIG. 14 shows again the detector window 11 on the helix cylinder rolled out on the plane of the sheet. However, this time it is overlaid with the same the detector window mapped onto the source cylinder arc 41. When rolled out on the sheet, this latter detector appears in FIG. 14 outlined as 141. Considering the geometry of FIG. 4, it might be more optimal to place the detector on the source cylinder arc 43 having the smallest possible radius close up to the object cylinder 13. However, since the geometry of such a detector would conform exactly with 141, we may discuss the geometry of 141 without loss of generality.

The detector 141 coincides with 11 in the middle but varies with γ so that the top-most and bottom-most point of the detector are found at $$z_{top} = \frac{v}{\omega R} \frac{\pi + 2\gamma}{\cos\gamma} \text{ and } z_{bottom} = \frac{v}{\omega R} \frac{\pi - 2\gamma}{\cos\gamma}, \quad (4)$$

respectively. The height H is then varying as $$H(\gamma) = z_{top} + z_{bottom} = \frac{v}{\omega R} \frac{2\pi}{\cos\gamma} = \frac{h}{\cos\gamma} \quad (5)$$

where h is the pitch as before. Thus, data which are captured on the source cylinder have to be resampled from the unevenly sloping detector area in FIG. 14 to the grid of the detector (also shown in FIG. 14), defined by vertical lines and evenly sloping lines with rhombus shaped detector elements. When projection data are resampled once more into parallel projections on the planar virtual detector in FIG. 5, the final grid pattern will be perfectly rectangular.

Figure 14:
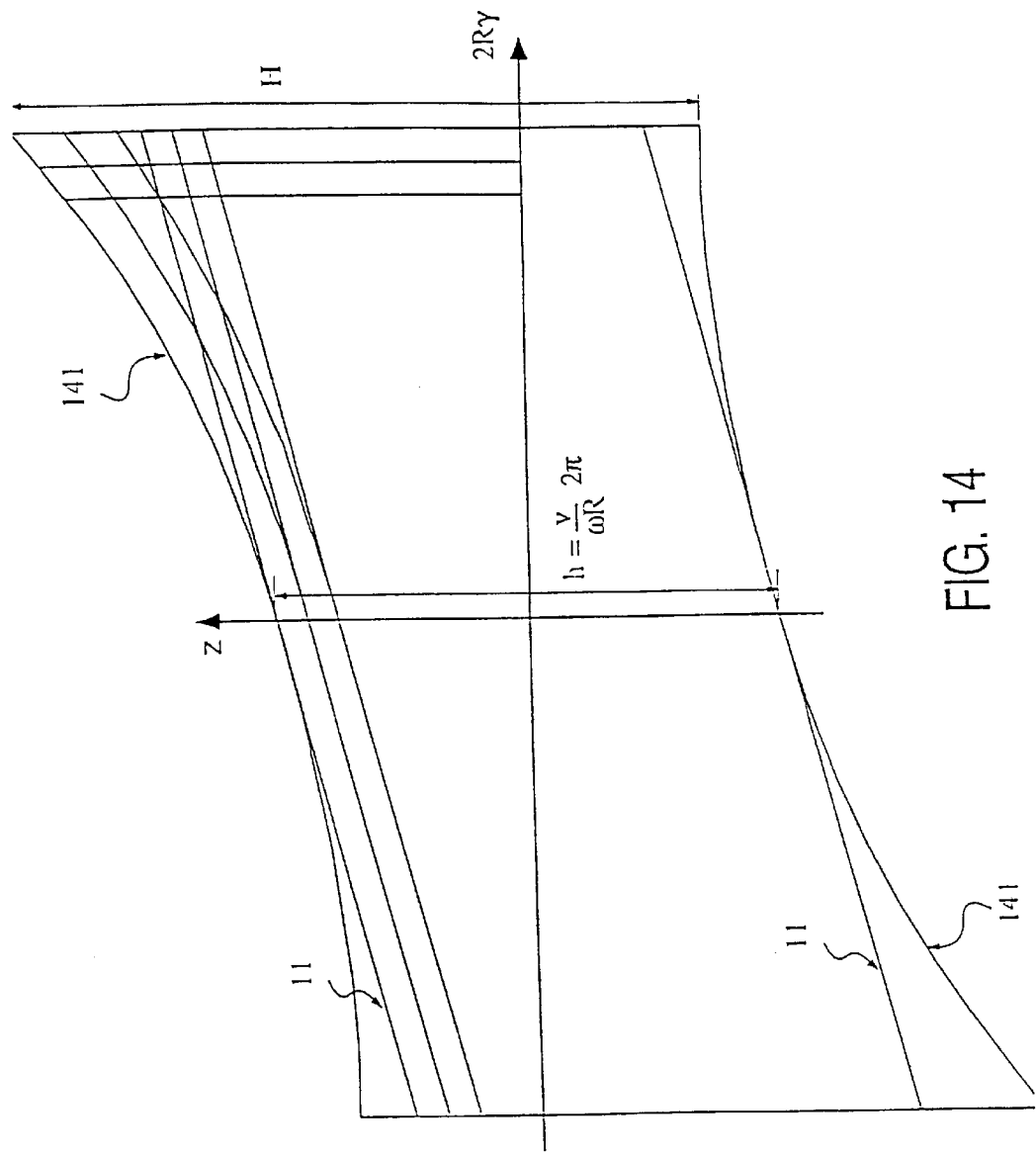
FIG. 14 depicts a detector window of the helix cylinder rolled out on a plane of a sheet.
Figure 15:
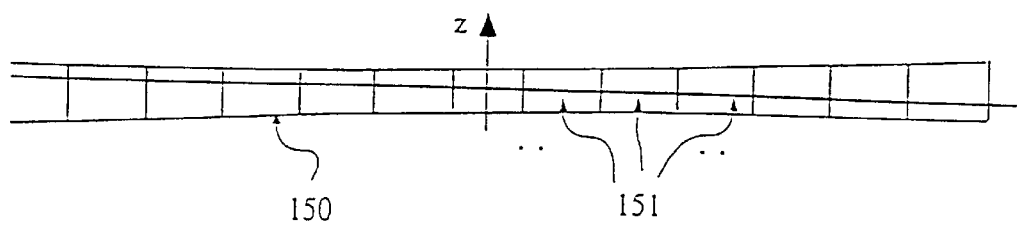
FIG. 15 is a depiction of the detector in FIG. 14 reduced in height to a single row of detector elements.

An important special case for the present invention is when the detector 141 (and the pitch) of FIG. 14 is reduced in height to a single row 150 of detector elements 151, which is shown in FIG. 15. We note that also in this special case will the height of the detector element increase with increasing fan angle as predicted by the above formula (5). Normally, the detector array in FIG. 15 would no longer be considered as a two-dimensional detector but a one-dimensional array detector. One-dimensional array detectors are used in existing helical fan-beam tomographs for which the state-of-the-art is represented by [King93]. The detector is normally placed on the surface of a source cylinder 41 although not designed as the one in FIG. 15. Instead, the detector elements are of constant height and they are not placed in a slanted fashion but horizontally straight on the source cylinder surface.

As a consequence, to secure sufficient data, either the height of the detector elements have to be increased, as in formula (3) which decreases the resolution in the z-direction, or the pitch of the helix has to be decreased with the same factor, which reduces the scanning efficiency and increases the dose compared to the present invention. The scanning will also acquire much redundant data so that the accompanying reconstruction procedure has to employ elaborate weighting factors to compensate for multiple exposure. Using the present invention with a detector designed and arranged accordingly, for instance as in FIG. 15, the data capture will be complete and free of redundancy and the reconstruction procedure can be simplified to contain the three steps rebinning, one-dimensional ramp filtering, and backprojection with constant magnification factor. All references cited herein are incorporated herein by reference in their entirety and for all purposes to the same extent as if each individual publication or patent or patent application was specifically and individually indicated to be incorporated by reference in its entirety for all purposes.

REFERENCES

[Dan97a] P. E. Danielsson, "Förfarande och anordning för tomografering", Swedish Patent application No 9700072-3, filed Jan. 14, 1997.

[Dan97b] P. E. Danielsson, Paul Edholm, Jan Eriksson, Maria Magnusson Seger, "*Towards Exact 3D-Reconstruction for Helical Scanning of Long Objects*", Conf. Record from 1997 Int. Meeting on Fully Three-Dimensional Image Reconstruction, Nemacollin, PA, Jun. 25–28, 1997.

[Feld84] L. A. Feldkamp, L. C. Davis, J. W. Kress, "*Practical Cone Beam Algorithms*", Journal of Optical Soc.Am. vol. A6, pp. 612–619, 1984.

[Wang93] G. Wang, T. H. Lin, P. C. Cheng, D. M. Shinozaki, "*A General Cone-Beam Reconstruction Algorithm*", IEEE Trans. on Medical Imaging, Vol. 12 pp. 486–496, 1993.

[Scha96] S. Schaller, T. Flohr, P. Steffen, "*A New Approximate Algorithm for Image Reconstruction in Cone-Beam Spiral CT at Small Cone Angles*", Conference Record, IEEE Medical Imaging Conference, pp. 1703–1709, November 1996, Anaheim, Calif.

[Scha97] S. Schaller, T. Flohr, P. Steffen, "*New Efficient Fourier-Reconstruction Method for Approximate Image Reconstruction in Spiral Cone-Beam CT at Small Cone Angles*", to be published in Proc. SPIE Med. Imaging Conf., Newport Beach, Calif., Feb.22–28, 1997.

[Tam95] K. C. Tam, "*Three-Dim. Computerized Tomography Scanning Method and System for Large Objects with Smaller Area Detectors*", U.S. Pat. No. 5,390,112, Feb. 14, 1995.

[Eber95] J. W. Eberhard; K. C. Tam, "*Helical and Circle Scan Region of Interest Computerized Tomography*", U.S. Pat. No. 5,463,666, Oct. 31, 1995.

[Gra87] P. Grangeat, "*Mathematical Framework of Cone-Beam 3D Reconstruction via the First Derivative of the Radon Transform*", in "*Mathematical Methods in Tomography*", G. T. Herman, A. K. Luis, F. Natterer (eds), Lecture Notes in Mathematics, Springer, 1991.

[King93] K. F. King, A. H. Lonn, C. R. Crawford, "*Computed Tomographic Image Reconstruction Method for Helical Scanning Using Interpolation of Partial Scans for Image Construction*", U.S. Pat. No. 5,270,923, Dec. 14, 1993.

What is claimed is:

1. A method for three-dimensional tomographic imaging of long objects, including the steps of:

subjecting the long object to be imaged to simultaneous translation and rotation relative to a cone-beam ray source and a two-dimensional detector limited to a window opposite to the cone-beam ray source, where this window is constrained to correspond to a surface area shaped as a parallelogram attached to a cylinder centered at an axis of rotation and passing through the cone-beam ray source, defining a height of the window measured along the length of the cylinder to equal a pitch of a helix and a width of the window such that a maximum width of the long object to be reconstructed is covered, determining an upper and lower boundary of the window to coincide with two consecutive turns of the source path relative to the fixed long object, and carrying out a reconstruction procedure comprising the steps of:

pre-weighting with a factor that depends on an angle of a ray that gave rise to a specific detector value, filtering with a ramp-filter horizontally or near horizontally across the detector, and back projecting with a magnification factor along the direction of a plurality of rays that gave rise to a plurality of original detector values, wherein the actual pre-weighting, the actual filter design, and the actual magnification factor depend on the physical embodiment given to the detector and a step of rebinning that has been employed with the detected data.

2. A method for three-dimensional tomographic imaging of long objects, including the steps of:

subjecting the long object to be investigated to simultaneous translation and rotation relative to a cone-beam ray source and a two-dimensional detector limited to a window opposite to the cone-beam ray source, where this window is constrained to correspond to a surface area shaped as a parallelogram attached to a cylinder centered at an axis of rotation and passing through the cone-beam ray source, defining a height of the window measured along the length of the cylinder to equal a pitch of a helix and a width of the window such that a maximum width of the long object to be reconstructed is covered, and determining an upper and lower boundary of the window to coincide with two consecutive turns of the source path relative to the fixed long object, and carrying out a reconstruction procedure comprising the steps of:

conducting, for each incoming cone-beam projection, rebinning to parallel projections as seen along the rotation axis, locating and resampling the rebinned data to a virtual detector plane on the rotation axis, ramp-filtering along all horizontal rows in the detector plane, and back-projecting in the direction of the original rays using a constant magnification factor.

3. A method for three-dimensional tomographic imaging of long objects, including the steps of:

subjecting one of the long objects to be investigated to simultaneous translation and rotation relative to a cone-beam ray source and a two-dimensional detector limited to a window opposite to the cone-beam ray source, where the window is constrained to correspond to a surface area shaped as a parallelogram attached to a cylinder centered at an axis of rotation and passing through the cone-beam ray source, defining a height of the window measured along the length of the cylinder to equal a pitch of a helix and a width of the window such that a maximum width of the long object to be reconstructed is fully covered, and determining an upper and lower boundary of the window to coincide with two consecutive turns of the source path relative to the fixed long object, and carrying out a reconstruction procedure comprising the steps of:

rebinning each incoming cone-beam projection to parallel projections as seen along the rotation axis, locating and resampling the rebinned data to a virtual detector plane in the rotation axis, and reconstructing one horizontal slice at a time using generalized projections and Fourier transform technique.

4. Arrangement and method for three-dimensional tomographic imaging of long objects as in claim 1, characterized by an effective detector area that has an extension which correspond to the area exposed through the aforementioned window but is physically shaped in a different way and placed in a different position.

5. Arrangement and method for three-dimensional tomographic imaging of long objects as in claim 4, characterized by a detector which is placed on a vertical plane.

6. Arrangement and method for three-dimensional tomographic imaging of long objects as in claim 4, characterized by a detector which is placed on the surface of a cylinder with a vertical axis on the source S.

7. Arrangement and method for three-dimensional tomographic imaging of long objects as in claim 4, characterized by a detector which is placed on the surface of a sphere centered on the source S.

8. Arrangement and method for three-dimensional tomographic imaging of long objects as in claim 4, characterized by a detector which is placed on the surface of a cylinder, which is on the source and tangential to the helix cylinder.

9. Arrangement and method for three-dimensional tomographic imaging of long objects as in claim 4, characterized by a detector consisting of one single row of detector elements.

10. Arrangement and method for three-dimensional tomographic imaging of long objects as in claim 2, characterized by an effective detector area that has an extension which correspond to the area exposed through the aforementioned window but is physically shaped in a different way and placed in a different position.

11. Arrangement and method for three-dimensional tomographic imaging of long objects as in claim 3, characterized by an effective detector area that has an extension which correspond to the area exposed through the aforementioned window but is physically shaped in a different way and placed in a different position.

* * * * *